(12) United States Patent
Okamoto et al.

(10) Patent No.: US 12,162,833 B2
(45) Date of Patent: Dec. 10, 2024

(54) ISOBUTYRIC ACID ESTER COMPOUND HAVING N-BUTYRYLOXY AT α-POSITION, PERFUME COMPOSITION, AND USE AS PERFUME

(71) Applicant: MITSUBISHI GAS CHEMICAL COMPANY, INC., Chiyoda-ku (JP)

(72) Inventors: Atsushi Okamoto, Niigata (JP); Umi Yokobori, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 686 days.

(21) Appl. No.: 17/433,028

(22) PCT Filed: Feb. 18, 2020

(86) PCT No.: PCT/JP2020/006278
§ 371 (c)(1),
(2) Date: Aug. 23, 2021

(87) PCT Pub. No.: WO2020/175241
PCT Pub. Date: Sep. 3, 2020

(65) Prior Publication Data
US 2022/0153681 A1 May 19, 2022

(30) Foreign Application Priority Data
Feb. 27, 2019 (JP) ................. 2019-034484

(51) Int. Cl.
*C07C 69/675* (2006.01)
*C11B 9/00* (2006.01)

(52) U.S. Cl.
CPC .......... *C07C 69/675* (2013.01); *C11B 9/0015* (2013.01)

(58) Field of Classification Search
None
See application file for complete search history.

(56) References Cited

U.S. PATENT DOCUMENTS

| | | | |
|---|---|---|---|
| 3,368,943 A | 2/1968 | Gilbert et al. | |
| 4,668,433 A | 5/1987 | Ochsner | |
| 2011/0097291 A1 | 4/2011 | Vial et al. | |
| 2016/0130526 A1 | 5/2016 | Vial | |
| 2021/0269743 A1* | 9/2021 | Okamoto | ................ C07C 69/67 |

FOREIGN PATENT DOCUMENTS

| | | |
|---|---|---|
| CN | 1275121 A | 11/2000 |
| CN | 1714067 A | 12/2005 |
| CN | 102046587 A | 5/2011 |
| CN | 105378045 A | 3/2016 |
| JP | 8-113795 A | 5/1996 |
| JP | 2011-524437 A | 9/2011 |
| WO | WO 00/14051 A1 | 3/2000 |
| WO | WO 2020/004464 A1 | 1/2020 |
| WO | WO 2020/004465 A1 | 1/2020 |
| WO | WO 2020/004466 A1 | 1/2020 |

OTHER PUBLICATIONS

International Search Report issued May 12, 2020 in PCT/JP2020/006278 filed Feb. 18, 2020, 2 pages.
Ruechardt, C., et al., "Zur ambivalenten reaktivitaet von α-acyloxycarbonsaeurechloriden", Chem. Ber., vol. 108, No. 10, 1975, pp. 3224-3242.
"Gosei Koryo: Kagaku to Shohin Chishiki, zoho shimban (Synthetic fragrance: chemistry and product knowledge, new enlarged edition)", The Chemical Daily Co. Ltd., 2016, pp. 580-582, 4 total pages.

* cited by examiner

*Primary Examiner* — Jessica Whiteley
(74) *Attorney, Agent, or Firm* — Oblon, McClelland, Maier & Neustadt, L.L.P.

(57) ABSTRACT

A compound, represented by Formula (1): wherein, in Formula (1), R represents a linear, branched, or cyclic alkyl group having 1 to 4 carbon atoms.

20 Claims, No Drawings

ISOBUTYRIC ACID ESTER COMPOUND HAVING N-BUTYRYLOXY AT α-POSITION, PERFUME COMPOSITION, AND USE AS PERFUME

CROSS-REFERENCE TO RELATED APPLICATIONS

This application is a national stage application of International Application No. PCT/JP2020/006278, filed Feb. 18, 2020, which is based upon and claims the benefit of priority to Japanese Patent Application No. 2019-034484, filed Feb. 27, 2019. The entire contents of these applications are incorporated herein by reference.

TECHNICAL FIELD

The present invention relates to isobutyric ester compounds having a n-butyryloxy group at the α-position, fragrance compositions, and use as a fragrance.

BACKGROUND ART

Some isobutyric esters are known to be compounds useful as fragrances. For example, Non-Patent Document 1 describes that various isobutyric esters are mainly used as flavors, and all of the following isobutyric esters are flavor materials having a fruit scent; specifically, methyl isobutyrate gives a sweet apricot-like scent, propyl isobutyrate gives a thick pineapple-like scent, butyl isobutyrate gives a fresh apple- and banana-like scent, and isoamyl isobutyrate gives a sweet apricot- and pineapple-like scent.

Additionally, Patent Document 1 discloses that, as an isobutyric ester having a bond with oxygen at α-position, a linear or branched alkyl ester of α-alkoxyisobutyric acid, the alkyl ester having 4 to 12 carbon atoms, is useful as a fragrance, and n-hexyl α-ethoxyisobutyrate has a lavender-like aroma.

CITATION LIST

Patent Documents

Patent Document 1: U.S. Pat. No. 3,368,943

Non-Patent Documents

Non-Patent Document 1: "Gosei Koryo: Kagaku to Shohin Chishiki, zoho shimban (Synthetic fragrance: chemistry and product knowledge, new enlarged edition)", The Chemical Daily Co. Ltd., 2016, 580 to 582

SUMMARY OF INVENTION

Technical Problem

An object to be solved by the present invention is to provide an isobutyric ester compound having a n-butyryloxy group at the α-position, useful as a fragrance and a fragrance ingredient. Further, an object to be solved by the present invention is to provide a fragrance composition containing the compound as an active ingredient and use of the compound as a fragrance.

Solution to Problem

The present inventors have synthesized various compounds and have made diligent research of the aromas thereof. Thus, the present inventors discovered that particular ester compounds of isobutyric acid having a n-butyryloxy group at the α-position are useful as fragrances and fragrance ingredients.

That is, the present invention is as follows.

<1> A compound, represented by Formula (1):

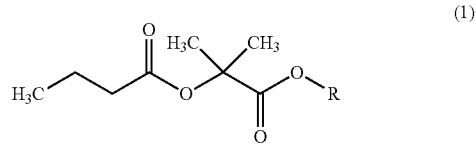

wherein, in Formula (1), R represents a linear, branched, or cyclic alkyl group having 1 to 4 carbon atoms.

<2> The compound according to <1>, wherein, in Formula (1), R is selected from the group consisting of a methyl group, an ethyl group, a n-propyl group, an isopropyl group, a n-butyl group, and an isobutyl group.

<3> The compound according to <1> or <2>, wherein, in Formula (1), R is a methyl group.

<4> The compound according to <1> or <2>, wherein, in Formula (1), R is an ethyl group.

<5> The compound according to <1> or <2>, wherein, in Formula (1), R is an n-propyl group.

<6> The compound according to <1> or <2>, wherein, in Formula (1), R is an isopropyl group.

<7> The compound according to <1> or <2>, wherein, in Formula (1), R is a n-butyl group.

<8> The compound according to <1> or <2>, wherein, in Formula (1), R is an isobutyl group.

<9> A fragrance composition comprising a compound described in any one of <1> to <8> as an active ingredient.

<10> Use of the compound described in any one of <1> to <8> as a fragrance.

<11> The use according to <10>, wherein the compound described in any one of <3>, <4>, and <6> imparts a damascone-like fruity-tone, floral-tone, or woody-tone scent.

Advantageous Effects of Invention

According to the present invention, it is possible to provide an isobutyric ester compound having a n-butyryloxy group at the α-position, useful as a fragrance and a fragrance ingredient. Furthermore, according to the present invention, it is possible to provide a fragrance composition containing the compound as an active ingredient and use of the compound as a fragrance.

DESCRIPTION OF EMBODIMENTS

[Compound Represented by Formula (1)]

A compound according to the present invention is represented by Formula (1) below. The compound represented by Formula (1) below is also referred to as the "isobutyric ester according to the present invention" or the "compound according to the present invention".

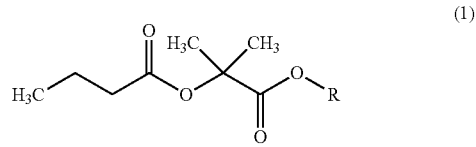

In Formula (1), R represents a linear, branched, or cyclic alkyl group having 1 to 4 carbon atoms.

Specific examples of R include a methyl group, an ethyl group, a n-propyl group, an isopropyl group, a n-butyl group, an isobutyl group (2-methylpropyl group), a sec-butyl group (1-methylpropyl group), a tert-butyl group, a cyclopropyl group, and a cyclobutyl group.

When R has an asymmetric carbon, the compound according to the present invention may include only one of optical isomers derived therefrom, or may be a mixture including a plurality of optical isomers in any proportion.

The compound represented by Formula (1) is a novel compound.

The isobutyric esters of the present invention represented by Formula (1) are useful as fragrances and fragrance ingredients and exhibit aromas such as floral-tone, green-tone, fruity-tone, and the like.

Particularly preferably, R is a methyl group.
Particularly preferably, R is an ethyl group.
Particularly preferably, R is a n-propyl group.
Particularly preferably, R is an isopropyl group.
Particularly preferably, R is a n-butyl group.
Particularly preferably, R is an isobutyl group.

In the present invention, examples of a compound represented by the Formula (1) include a compound represented by any of Formulas (1-1) to (1-10) below, and particularly preferable compounds include a compound represented by any of Formulas (1-1) to (1-6) below.

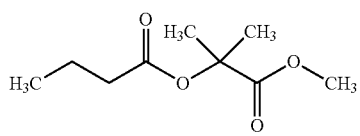

(1-1)

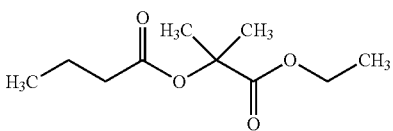

(1-2)

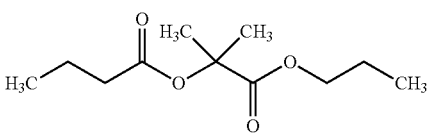

(1-3)

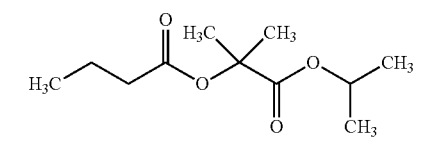

(1-4)

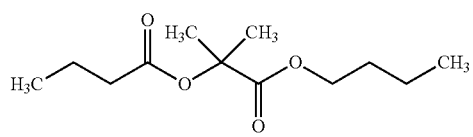 [SMILES: CCCCOC(=O)C(C)(C)OC(=O)CCC]

(1-5)

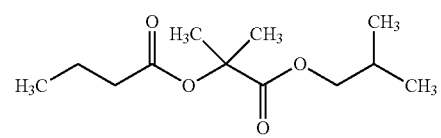 [SMILES: CCCC(=O)OC(C)(C)C(=O)OCC(C)C]

(1-6)

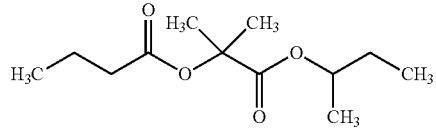

(1-7)

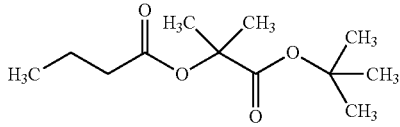

(1-8)

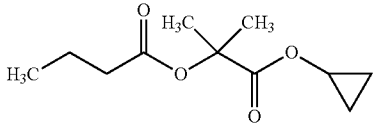

(1-9)

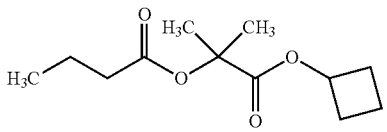

(1-10)

In recent years, there is a trend to focus more on the toxicity and environmental impact of chemicals, and fragrances or fragrance compositions are no exception. There is an increase in the number of cases where a fragrance which has been used in the past is severely restricted in usage conditions or is prohibited from use due to their sensitization properties to a human body, tendency to accumulate in the environment, and the like. Thus, there is a strong demand for a fragrance and a fragrance composition having a lower environmental impact. Accordingly, the fragrance ingredient preferably has excellent biodegradability.

The compound according to the present invention contains a compound excellent in biodegradability, and from the perspective of biodegradability, R is preferably a group selected from the group consisting of a methyl group, an ethyl group, a n-propyl group, an isopropyl group, a n-butyl group, and an isobutyl group.

The isobutyric ester according to the present invention is useful as a fragrance because the compound has an excellent aroma as described below. Generally, a fragrance is rarely used alone, and often used in a fragrance formulation (fragrance composition) produced by formulating a plurality of fragrances in accordance with the purpose. The isobutyric ester according to the present invention is useful as a fragrance which is to be blended in a fragrance formulation (fragrance composition) (also referred to as a "fragrance ingredient"). As the fragrance, one of the compounds represented by Formula (1) above may be used alone or two or more of the compounds may be used in combination.

Additionally, the compound according to the present invention may include a small amount of impurities, by-products, contaminants, and the like as long as the effects of the present invention are not compromised.

The isobutyric ester according to the present invention represented by Formula (1) has an aroma of floral-tone, green-tone, fruity-tone, or like, and also is excellent in diffusivity. Further, the isobutyric ester according to the present invention represented by any of Formulas (1-1), (1-2), and (1-4) has a damascone-like fruity-tone, floral-tone, or woody-tone aroma, and also is excellent in diffusivity.

The isobutyric ester according to the present invention may be used alone as a fragrance and added to various perfumery and cosmetics, healthcare and sanitary materials as well as medicinal supplies, household goods, foods, and the like to thereby impart an aroma thereto. Alternatively, the isobutyric ester according to the present invention may be mixed with another fragrance ingredient or the like to prepare a fragrance composition (fragrance formulation) described below, which may be blended into a variety of products to impart an aroma. Among these, from the perspective of obtaining an intended aroma, it is preferred that the compound according to the present invention be blended in a fragrance composition as a fragrance ingredient and the fragrance composition be blended in a product to perfume the product.

[Fragrance Composition]

The fragrance composition (fragrance formulation) according to the present invention contains the isobutyric ester according to the present invention as an active ingredient. Note that the isobutyric ester according to the present invention is not particularly limited as long as it contains at least one isobutyric ester according to the present invention, and two or more isobutyric esters may be contained.

The fragrance composition according to the present invention is only required to contain the isobutyric ester according to the present invention as an active ingredient, and other ingredients are not particularly limited. However, the fragrance composition preferably contains another fragrance ingredient (hereinafter, also referred to as a "known fragrance").

Note that the "fragrance composition (fragrance formulation)" is a composition that is added to various perfumery and cosmetics, medicinal supplies, foods, beverages, and the like to impart an aroma thereto, or a composition that is used as it is in a perfume or the like. The fragrance composition may contain an additive such as a solvent, as required, in addition to the known fragrance.

The amount of the isobutyric ester according to the present invention blended depends on the type of the isobutyric ester according to the present invention, the type of aroma intended, the intensity of the aroma, and the like. The amount of the isobutyric ester according to the present invention represented by Formula (1) in the fragrance composition is preferably 0.001 mass % or greater, more preferably 0.01 mass % or greater, even more preferably 0.1 mass % or greater, preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals such as acetoaldehyde ethylphenylpropyl acetal, citraldiethyl acetal, phenylacetoaldehyde glycerin acetal, and ethylacetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, *eucalyptus*, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant; a coloring agent, and the like.

The isobutyric ester according to the present invention represented by Formula (1), which has an aroma of a floral tone, a green tone, a fruity tone, or the like, can impart a more natural floral tone, green tone, or fruity tone when combined with a known fragrance. Thus, the isobutyric ester is usefully added to various perfumery and cosmetics, healthcare and sanitary materials as well as to medicinal supplies, household goods, foods, and the like to thereby impart an aroma thereto. The isobutyric ester according to the present invention represented by any of Formulas (1-1), (1-2), and (1-4) are usefully combined with a known fragrance or the like, thereby imparting an aroma because the isobutyric ester has a damascone-like fruity-tone, floral-tone, or woody-tone aroma.

Examples of products to which a fragrance composition containing the isobutyric esters according to the present invention represented by Formula (1) can be added to impart an aroma and improve the aroma of the object include various products such as perfumery and cosmetics, health and sanitary materials, miscellaneous goods, beverages, foods, quasi-pharmaceutical products, and medicinal supplies. The fragrance composition can be used as an aroma component in, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

[Method for Producing Isobutyric Ester of Present Invention]

The production method of the isobutyric ester according to the present invention represented by Formula (1) is not particularly limited and may be appropriately selected from known methods and used.

Examples thereof include a method including reacting an α-hydroxyisobutyric ester with an acylating agent in the presence or absence of a catalyst to acylate the hydroxyl group at the α-position. Examples of the acylating agent to be used include carboxylic acids such as butyric acid, carboxylic anhydrides such as butyric anhydride, carboxylic halides such as butyryl chloride and butyryl bromide, and ketene compounds such as ethyl ketene. In addition, two or more acylating agents selected from these may be used in combination at any ratio.

The reaction formula when a carboxylic acid, a carboxylic acid anhydride, or a carboxylic acid halide is used is shown as Formula (2) below.

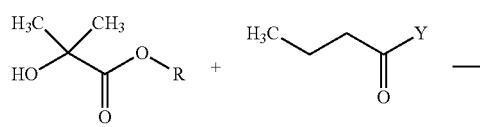

(2)

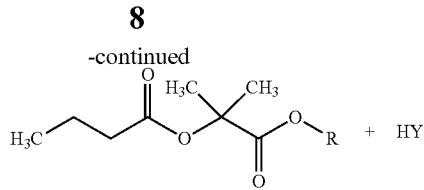

In Formula (2), R represents a linear, branched, or cyclic alkyl group having 1 to 4 carbon atoms. Y depends on the type of the acylating agent and represents, for example, a hydroxyl group, a n-butyryloxy group, chlorine, bromine, iodine, or the like.

The reaction formula when a ketene compound is used is shown as Formula (3) below.

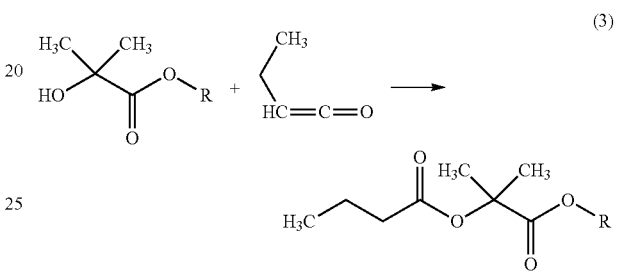

(3)

In Formula (3), R represents a linear, branched, or cyclic alkyl group having 1 to 4 carbon atoms.

Further, a target α-n-butyryloxyisobutyric ester can be produced by transesterifying an α-n-butyryloxyisobutyric ester with an alcohol of different kinds in the presence of a catalyst. The reaction formula for this reaction is shown as Formula (4) below.

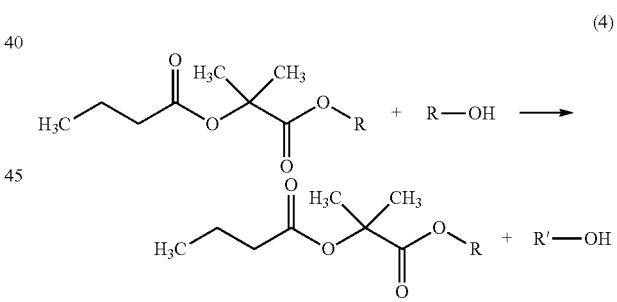

(4)

In Formula (4), R represents a linear, branched, or cyclic alkyl group having 1 to 4 carbon atoms. R' is not particularly limited as long as it is an alkyl group different from R.

Similarly, a target α-n-butyryloxyisobutyric ester can be produced by esterifying an α-n-butyryloxyisobutyric acid with an alcohol in the presence of a catalyst. The reaction formula for this reaction is shown as Formula (5) below.

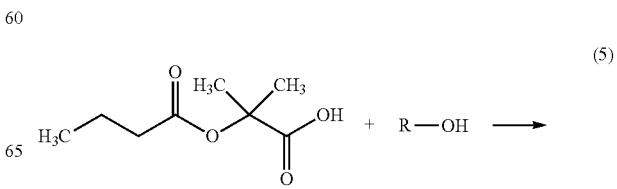

(5)

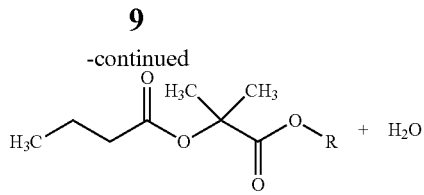

In Formula (5), R represents a linear, branched, or cyclic alkyl group having 1 to 4 carbon atoms.

Known catalysts, reaction methods, reaction conditions, and reaction apparatuses can be used as the catalyst, reaction method, reaction conditions, reaction apparatuses, and the like to be used for these reactions, and there are no particular limitation thereon. In addition, as a method for purifying the obtained compound of Formula (1), a known purification method can be used, and there is no limitation thereon.

EXAMPLES

Hereinafter, the present invention will be described in further detail with reference to examples, but the present invention is not limited to these examples.

The reaction performance was evaluated according to the following expression.

Reaction yield (%)=[(number of moles of product ester in reaction solution)/(number of moles of raw material ester in solution fed)]×100%

<Gas Chromatography (GC) Analysis Conditions>
Apparatus: GC-2010 (available from Shimadzu Corporation, trade name)
Detector: FID
Column: DB-1 (capillary column available from J&W Scientific, Inc., trade name) (0.25 mmφ×60 m×0.25 μm)
<NMR Spectrum Analysis>
Identification of the ester was performed by $^1$H-NMR measurement and $^{13}$C-NMR measurement. The measurement conditions are shown below.
Apparatus: ECA500 (available from JEOL Ltd., trade name)
[$^1$H-NMR]
Nuclide: $^1$H
Measurement frequency: 500 MHz
Measurement sample: 5% CDCl$_3$ solution
[$^{13}$C-NMR]
Nuclide: $^{13}$C
Measurement frequency: 125 MHz
Measurement sample: 5% CDCl$_3$ solution
<Gas Chromatograph-Mass Spectrometry (GC-MS Analysis)>
Identification of the compounds was also performed by determining the molecular weight by GC-MS measurement (chemical ionization method [CI+], high resolution mass spectrometry [millimass]). The measurement conditions are shown below.
GC apparatus: Agilent 7890A (available from Agilent Technologies, trade name)
GC Measurement Conditions
Column: DB-1 (capillary column available from J&W Scientific, Inc., trade name) (0.25 mmφ×30 m×0.25 μm)
MS apparatus: JMS-T100GCV (available from JEOL Ltd., trade name)
MS measurement conditions: chemical ionization method
Detector conditions: 200 eV, 300 μA
Reagent gas: isobutane The Exact. Mass values of fragments detected in the protonated state by the chemical ionization method and the chemical composition formula thus attributed were described.
<Product Isolation by Chromatograph Method>
Materials described below were used for product isolation by a chromatograph method.
Filler: Wakogel C-200 (available from Wako Pure Chemical Industries, Ltd., trade name)
Development solvent: ethyl acetate-hexane Example 1: Synthesis of Methyl α-n-butyryloxyisobutyrate 20.0 g of methyl α-hydroxyisobutyrate (available from Mitsubishi Gas Chemical Company, Inc.), 29.4 g of butyric anhydride (available from Wako Pure Chemical Industries, Ltd.), 13.6 g of pyridine (available from Wako Pure Chemical Industries, Ltd.), and 2.1 g of 4-dimethylaminopyridine (available from Wako Pure Chemical Industries, Ltd.) were loaded in a 200 ml glass round bottom flask equipped with a condenser and a stirrer, and reacted under stirring at room temperature to 40° C. for 24 hours. From the GC analysis of the reaction solution, it was confirmed that methyl α-hydroxyisobutyrate was completely consumed by the reaction with butyric anhydride and that methyl α-n-butyryloxyisobutyrate was obtained at a reaction yield of 93% by the reaction of the following formula (7). Then, a washing operation was performed three times with a 10% aqueous solution of sodium hydrogen carbonate and twice with a saturated aqueous solution of sodium chloride. The washed product was dried over magnesium sulfate. Thereafter, 21.2 g of methyl α-n-butyryloxyisobutyrate (purity by GC analysis (hereinafter, also referred to as GC purity): >99.9%) was obtained by column chromatograph. The results of the NMR spectral analysis and GC-MS analysis of the product are shown below.

Methyl α-n-butyryloxyisobutyrate $^1$H NMR (500 MHz, CDCl$_3$) δ 0.96 (3H, t, J=7.5 Hz), 1.55 (6H, s), 1.65 (2H, sext, J=7.5 Hz) 2.29 (2H, t, J=7.5 Hz), 3.72 (3H, s)
$^{13}$C NMR (125 MHz, CDCl$_3$) δ13.46, 18.34, 24.59, 36.14, 52.27, 77.83, 172.65, 173.19
Exact. Mass 189.11383 (C$_9$H$_{16}$O$_4$, parent peak), 157.08676 (C$_8$H$_{12}$O$_3$)

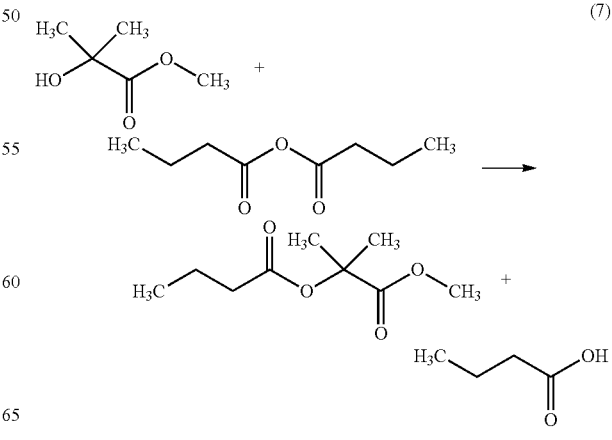

Reference Example 1: Synthesis of Ethyl α-hydroxyisobutyrate

In a 300 ml glass flask equipped with a distillation tube, 56.7 g of methyl α-hydroxyisobutyrate (available from Mitsubishi Gas Chemical Company, Inc.), 33.2 g of ethanol (available from Wako Pure Chemical Industries, Ltd.), and 0.92 g of titanium tetraethoxide (available from Wako Pure Chemical Industries, Ltd.) were loaded. A transesterification reaction was performed under normal pressure with heating and refluxing. The reaction was performed for 96 hours while methanol produced was extracted out of the system. As a result, ethyl α-hydroxyisobutyrate was obtained at a reaction yield of 97%. After water was added to the reaction system to inactivate the catalyst, distillation was performed under reduced pressure to obtain 46.9 g of ethyl α-hydroxyisobutyrate (GC purity: 99.6%) as the fraction at 71 mmHg and 77° C.

Reference Examples 2 to 5: Synthesis of Various α-Hydroxyisobutyric Esters

Using the same reaction apparatus as in Reference Example 1, an appropriate amount of methyl α-hydroxyisobutyrate (available from Mitsubishi Gas Chemical Company, Inc.) was transesterified with a different alcohol (n-propanol, isopropanol, n-butanol, isobutanol) in the presence of a suitable catalyst such as a titanium tetraalkoxide and/or sodium alkoxide, and in some cases in the co-presence of a solvent such as hexane or toluene, under appropriate reaction conditions with heating. The transesterification reaction was completed while methanol produced by the reaction was extracted out of the system by distillation or through azeotrope with a reaction solvent under the reaction conditions. The same separation operation as in Reference Example 1 was performed to obtain each of the following α-hydroxyisobutyric ester. The GC purity of the obtained isobutyric ester is also shown.

n-propyl α-hydroxyisobutyrate (GC purity: 99.8%)
Isopropyl α-hydroxyisobutyrate (GC purity: 99.6%)
n-butyl α-hydroxyisobutyrate (GC purity: 99.9%)
Isobutyl α-hydroxyisobutyrate (GC purity: 99.6%)

Example 2: Synthesis of Ethyl α-n-butyryloxyisobutyrate

Using a reaction apparatus similar to that of Example 1, a reaction was performed using ethyl α-hydroxyisobutyrate prepared in Reference Example 1, butyric anhydride (available from Wako Pure Chemical Industries, Ltd.), pyridine (available from Wako Pure Chemical Industries, Ltd.), and 4-dimethylaminopyridine (available from Wako Pure Chemical Industries, Ltd.) in appropriate amounts. The operation was performed in the same manner as in Example 1 to obtain ethyl α-n-butyryloxyisobutyrate (GC purity: 99.83%). The results of the NMR spectral analysis and GC-MS analysis of the product are shown below.

Ethyl α-n-butyryloxyisobutyrate $^1$H NMR (500 MHz, CDCl$_3$) δ 0.96 (3H, t, J=7.5 Hz), 1.25 (3H, t, J=7.0 Hz), 1.54 (6H, s), 1.65 (2H, sext, J=7.5 Hz), 2.29 (2H, t, J=7.5 Hz), 4.18 (2H, q, J=7.0 Hz)
$^{13}$C NMR (125 MHz, CDCl$_3$) δ13.51, 13.99, 18.37, 24.56, 36.17, 61.15, 77.90, 172.56, 172.67
Exact. Mass 203.13157 (C$_{10}$H$_{18}$O$_4$, parent peak), 157.08746 (C$_8$H$_{12}$O$_3$)

Examples 3 to 6: Synthesis of α-n-butyryloxyisobutyric Ester

Using a reaction apparatus similar to that of Example 2, a reaction was performed using each α-hydroxyisobutyric ester prepared in Reference Examples 2 to 5, butyric anhydride (available from Wako Pure Chemical Industries, Ltd.), pyridine (available from Wako Pure Chemical Industries, Ltd.), and 4-dimethylaminopyridine (available from Wako Pure Chemical Industries, Ltd.) in appropriate amounts. The operation was performed in the same manner as in Example 1 to obtain each of the following α-n-butyryloxyisobutyric esters with column chromatograph. The GC purity of the resulting esters and the results of NMR spectral analysis and GC-MS analysis are shown in combination.

Example 3: n-propyl α-n-butyryloxyisobutyrate

GC purity: 99.81%
$^1$H NMR (500 MHz, CDCl$_3$) δ 0.94 (3H, t, J=7.5 Hz), 0.96 (3H, t, J=7.5 Hz), 1.55 (6H, s), 1.61-1.69 (4H, m), 2.29 (2H, t, J=7.5 Hz), 4.08 (2H, t, J=6.5 Hz)
$^{13}$C NMR (125 MHz, CDCl$_3$) δ 10.29, 13.53, 18.34, 21.82, 24.62, 36.18, 66.76, 77.96, 172.56, 172.75
Exact. Mass 217.14467 (C$_{11}$H$_{20}$O$_4$, parent peak), 157.08749 (C$_8$H$_{12}$O$_3$)

Example 4: Isopropyl α-n-butyryloxyisobutyrate

GC purity: 99.96%
$^1$H NMR (500 MHz, CDCl$_3$) δ 0.97 (3H, t, J=7.5 Hz), 1.22 (6H, d, J=6.5 Hz), 1.53 (6H, s), 1.65 (2H, sext, J=7.5 Hz), 2.28 (2H, t, J=7.5 Hz), 5.03 (1H, sep, J=6.5 Hz)
$^{13}$C NMR (125 MHz, CDCl$_3$) δ 13.59, 18.42, 21.55, 24.53, 36.22, 68.57, 77.98, 172.15, 172.48
Exact. Mass 217.14709 (C$_{11}$H$_{20}$O$_4$, parent peak), 175.09776 (C$_8$H$_{14}$O$_4$)

Example 5: n-butyl α-n-butyryloxyisobutyrate

GC purity: 99.91%
$^1$H NMR (500 MHz, CDCl$_3$) δ 0.93 (3H, t, J=7.5 Hz), 0.96 (3H, t, J=7.5 Hz), 1.37 (2H, sext, J=7.5 Hz), 1.54 (6H, s), 1.58-1.69 (4H, m), 2.28 (2H, t, J=7.5 Hz), 4.12 (2H, t, J=6.5 Hz)
$^{13}$C NMR (125 MHz, CDCl$_3$) δ 13.54, 13.65, 18.35, 19.04, 24.61, 30.45, 36.19, 65.05, 77.96, 172.56, 172.77
Exact. Mass 231.16103 (C$_{12}$H$_{22}$O$_4$, parent peak), 157.08815 (C$_8$H$_{12}$O$_3$)

Example 6: Isobutyl α-n-butyryloxyisobutyrate

GC purity: 99.62%
$^1$H NMR (500 MHz, CDCl$_3$) δ 0.93 (6H, d, J=6.5 Hz), 0.96 (3H, t, J=7.5 Hz), 1.56 (6H, s), 1.65 (2H, sext, J=7.5 Hz), 1.94 (1H, m), 2.29 (2H, t, J=7.5 Hz), 3.90 (2H, d, J=6.5 Hz)
$^{13}$C NMR (125 MHz, CDCl$_3$) δ 13.57, 18.33, 19.00, 24.66, 27.65, 36.20, 71.24, 78.01, 172.56, 172.72
Exact. Mass 231.16303 (C$_{12}$H$_{22}$O$_4$, parent peak), 157.08976 (C$_8$H$_{12}$O$_3$)

The results of aroma evaluation performed by a perfumer for the various α-n-butyryloxyisobutyric esters obtained by the method described above are shown in Table 1.

TABLE 1

| Example | Structural formula | Aroma evaluation |
| --- | --- | --- |
| 1 | (structure) | Rose-like floral (damascone-like)<br>Spicy<br>Fruity |
| 2 | (structure) | Rose-like floral (damascone-like)<br>Spicy<br>Coconut-like fruity<br>Mint-like green |
| 3 | (structure) | Rose-like floral<br>Spicy<br>Mint-like green<br>Coconut-like fruity |
| 4 | (structure) | Rose-like floral (damascone-like)<br>Fruity<br>Mint-like green |
| 5 | (structure) | Banana-like fruity<br>Green<br>Coconut-like fruity |
| 6 | (structure) | Banana-like fruity<br>Mint-like green<br>Coconut-like fruity |

<Biodegradability Evaluation of Fragrance Material>

One of methods for evaluating biodegradability of a compound is the OECD test guideline 301 C. In accordance with the method, assessment of biodegradability is possible for the compound from the biochemical oxygen demand and the actual rate of oxygen uptake in an aqueous solution in which the compound and aerobic microorganisms coexist.

Calculation software "Biowin5" and "Biowin6" is known and used in a method for easily and accurately estimating from the chemical structure the probability of biodegradation of the compound in compliance with this test method.

The software is available to the public as one of modules of calculation software called "The Estimations Programs Interface for Windows version 4.1", created by the United States Environmental Protection Agency (EPA) for the purpose of evaluating the environmental effects of chemical substances, and is used in the compound classification for The Globally Harmonized System of Classification and Labelling of Chemicals (GHS) and the review of new chemical substances by the United States Environmental Protection Agency. This software was used to evaluate the difference in biodegradability between existing fragrance materials and the compounds according to the present invention.

(E)-α-damascone and (E)-β-damascenone, having a floral note, were selected as representative examples of existing fragrance materials similar to the compounds according to the present invention, and evaluated along with the compounds according to the present invention. The SMILES formulas used for input to the software and the output results of the probabilities of good degradability by "Biowin5 (linear prediction model)" and "Biowin6 (non-linear prediction model)" are shown in Tables 2 to 3. A larger value of the results indicates better degradability: for a value of 0.5 or greater, the compound was rated as having good degradability (symbol "A" in the table), and for a value of less than 0.5, the compound was rated as having low degradability (symbol "B" in the table).

From Table 2 to Table 3, the results obtained show that the compounds according to the present invention were expected to have better biodegradability as compared with (E)-α-damascone and (E)-β-damascenone, which were the existing fragrance materials similar to the compounds according to the present invention. The results indicated that the compounds according to the present invention are easily biodegraded after being released into the environment as fragrances, and thus exhibited a lower impact on the environment.

TABLE 2

| Example | Structural formula | SMILES | Biowin5 Degradation probability | Score | Biowin6 Degradation probability | Score |
|---|---|---|---|---|---|---|
| 1 | | COC(C(C)(C)OC(CCC)=O)=O | 1.008 | A | 0.965 | A |
| 2 | | CC(C(OCC)=O)(C)OC(CCC)=O | 1.015 | A | 0.966 | A |
| 3 | | CC(C(OCCC)=O)(C)OC(CCC)=O | 1.023 | A | 0.967 | A |
| 4 | | CC(C(OC(C)C)=O)(C)OC(CCC)=O | 0.874 | A | 0.919 | A |
| 5 | | CC(C(OCCCC)=O)(C)OC(CCC)=O | 1.031 | A | 0.968 | A |
| 6 | | CC(C(OCC(C)C)=O)(C)OC(CCC)=O | 0.882 | A | 0.921 | A |

TABLE 3

| Comparative Example | Structural formula | SMILES | Biowin5 Degradation probability | Score | Biowin6 Degradation probability | Score |
|---|---|---|---|---|---|---|
| 1 | ((E)-alpha-damascone) | CC1(C)C(C(/C=C/C)=O)C(C)=CCC1 | 0.398 | B | 0.216 | B |
| 2 | ((E)-beta-damascenone) | CC1(C)C(C(/C=C/C)=O)=C(C)C=CC1 | 0.378 | B | 0.213 | B |

Example 7: LILY BOUQUET-type Fragrance Composition

A fragrance composition was formulated by adding 5.0 parts by mass of the isopropyl α-n-butyryloxyisobutyrate obtained in Example 4 to 95.0 parts by mass of a fragrance composition having a composition shown in Table 4.

According to the aroma evaluation by a perfumer, addition of the isopropyl α-n-butyryloxyisobutyrate of Example 4 to the fragrance composition having the composition described in Table 4 added rose-like floralness and fruitiness, and a floral feeling having gorgeous sweetness and expansion was achieved. As a result, there was provided a more natural and elegant fragrant muguet-tone aroma fragrance composition having rose-like floral sweetness and fruitiness imparted.

The aroma of this fragrance composition seems to be suitable for perfuming shampoos, skin lotions, skin creams, emulsions, softeners, soaps, and the like.

TABLE 4

| Blend ingredients | parts by mass |
| --- | --- |
| HIDROXY CITRONELLAL | 10.0 |
| JASMIN BASE A-15363/FC (Yamamoto Perfumery) | 7.0 |
| ISO E SUPER (IFF) | 8.0 |
| AMBRETTOLIDE (IFF) | 0.8 |
| BENZYL ACETATE | 1.0 |
| BENZYL PROPIONATE | 0.6 |
| CITRONELLA OIL | 0.1 |
| CITRONELLOL | 8.0 |
| CYCLAMEN ALDEHYDE | 0.7 |
| GALAXOLIDE 50BB (IFF) | 4.5 |
| GERANIOL | 6.5 |
| HEXYL CINNAMIC ALDEHYDE | 1.5 |
| INDOFLOR CRYSTAL (Symrise) | 0.5 |
| LILY ALDEHYDE | 20.0 |
| LINALOOL | 2.5 |
| HEDION (Firmenich) | 10.0 |
| NEROL | 3.0 |
| Phenyl acetaldehyde dimethyl acetal | 0.3 |
| Phenylethyl alcohol | 10.0 |
| Total | 95.0 |

INDUSTRIAL APPLICABILITY

An isobutyric ester compound having a n-butyryloxy group at the α-position according to the present invention has an excellent aroma and is expected to be used itself as a fragrance. Additionally, use of the compound as a fragrance ingredient can provide a fragrance composition excellent in aroma properties. The composition, when blended in a variety of products, exhibits desired perfuming properties.

Furthermore, it was shown that the compounds obtained in Examples each have excellent biodegradability and a low impact on the environment and are suitable for use.

The invention claimed is:

1. A compound of the following formula (1),

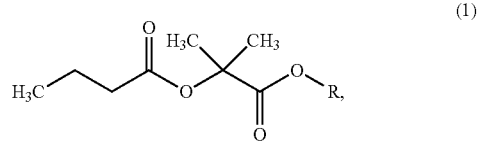

wherein R is a linear, branched, or cyclic alkyl group having 1 to 4 carbon atoms.

2. The compound according to claim 1, wherein R is selected from the group consisting of a methyl group, an ethyl group, a n-propyl group, an isopropyl group, a n-butyl group, and an isobutyl group.

3. The compound according to claim 1, wherein R is a methyl group.

4. The compound according to claim 1, wherein R is an ethyl group.

5. The compound according to claim 1, wherein R is n-propyl group.

6. The compound according to claim 1, wherein R is an isopropyl group.

7. The compound according to claim 1, wherein R is a n-butyl group.

8. The compound according to claim 1, wherein R is an isobutyl group.

9. A fragrance composition, comprising:
an active ingredient comprising the compound of claim 1.

10. A fragrance, comprising:
the compound of claim 1.

11. A fragrance, comprising: the compound of claim 3, wherein the compound imparts a damascone-like fruity-tone, floral-tone, or woody-tone scent.

12. A fragrance composition, comprising:
an active ingredient comprising the compound of claim 2.

13. A fragrance, comprising:
the compound of claim 2.

14. A fragrance, comprising:
the compound of claim 4,
wherein the compound imparts a damascone-like fruity-tone, floral-tone, or woody-tone scent.

15. A fragrance, comprising:
the compound of claim 6,
wherein the compound imparts a damascone-like fruity-tone, floral-tone, or woody-tone scent.

16. A fragrance composition, comprising:
an active ingredient comprising the compound of claim 3.

17. A fragrance composition, comprising:
an active ingredient comprising the compound of claim 4.

18. A fragrance composition, comprising:
an active ingredient comprising the compound of claim 5.

19. A fragrance composition, comprising:
an active ingredient comprising the compound of claim 6.

20. A fragrance composition, comprising:
an active ingredient comprising the compound of claim 7.

* * * * *